US00PP21639P2

(12) United States Plant Patent
Takahashi

(10) Patent No.: US PP21,639 P2
(45) Date of Patent: Jan. 18, 2011

(54) *VERBENA* PLANT NAMED 'AKIV98-01'

(50) Latin Name: *Verbena hybrida*
Varietal Denomination: AKIV98-01

(75) Inventor: Akiko Takahashi, Higashiomi (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 12/653,192

(22) Filed: Dec. 9, 2009

(51) Int. Cl.
*A01H 5/00* (2006.01)

(52) U.S. Cl. ..... Plt./308

(58) Field of Classification Search ..... Plt./308
See application file for complete search history.

*Primary Examiner*—Annette H Para
(74) *Attorney, Agent, or Firm*—C. A. Whealy

(57) ABSTRACT

A new and distinct cultivar of *Verbena* plant named 'AKIV98-01', characterized by its low and outwardly spreading plant habit; vigorous growth habit; freely branching habit; freely flowering habit; large coral red-colored flowers that are held above and beyond the foliage; and resistance to Powdery Mildew.

1 Drawing Sheet

Botanical designation: *Verbena hybrida.*
Cultivar denomination: 'AKIV98-01'.

BACKGROUND OF THE INVENTION

The present invention relates to a new and distinct cultivar of *Verbena* plant, botanically known as *Verbena hybrida,* and hereinafter referred to by the name 'AKIV98-01'.

The new *Verbena* plant is a product of a planned breeding program conducted by the Inventor in Shiga, Japan. The objective of the breeding program is to create new freely flowering *Verbena* cultivars with large flowers and resistance to Powdery Mildew.

The new *Verbena* plant originated from a cross-pollination made by the Inventor on May 25, 2005 in Shiga, Japan of *Verbena peruviana* 'Sunvivaro', disclosed in U.S. Plant Pat. No. 13,724, as the female, or seed, parent with *Verbena hybrida* 'USBENAL17', disclosed in U.S. Plant Pat. No. 14,877, as the male, or pollen, parent. The new *Verbena* plant was discovered and selected by the Inventor as a single flowering plant within the progeny of the stated cross-pollination in a controlled environment in Shiga, Japan on Jun. 29, 2007.

Asexual reproduction of the new *Verbena* plant by terminal cuttings in a controlled environment in Shiga, Japan since June, 2007 has shown that the unique features of this new *Verbena* plant are stable and reproduced true to type in successive generations.

SUMMARY OF THE INVENTION

Plants of the new *Verbena* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'AKIV98-01'. These characteristics in combination distinguish 'AKIV98-01' as a new and distinct cultivar of *Verbena:*

1. Low and outwardly spreading plant habit.
2. Vigorous growth habit.
3. Freely branching habit.

4. Freely flowering habit.
5. Large coral red-colored flowers that are held above and beyond the foliage.
6. Resistant to Powdery Mildew.

Plants of the new *Verbena* can be compared to plants of the female parent, 'Sunvivaro'. Plants of the new *Verbena* differ primarily from plants of 'Sunvivaro' in the following characteristics:

1. Plants of the new *Verbena* are more upright than plants of 'Sunvivaro'.
2. Plants of the new *Verbena* have larger flowers than plants of 'Sunvivaro'.

Plants of the new *Verbena* can be compared to plants of the male parent, 'USBENAL17'. Plants of the new *Verbena* differ primarily from plants of 'USBENAL17' in the following characteristics:

1. Plants of the new *Verbena* do not stretch as much as plants of 'USBENAL17'.
2. Flower petals of plants of the new *Verbena* are more oblong than and not as rounded as flower petals of plants of 'USBENAL17'.

Plants of the new *Verbena* can be compared to plants of the *Verbena hybrida* 'Lan Depink', disclosed in U.S. Plant Pat. No. 15,741. In side-by-side comparisons conducted in Bonsall, Calif., plants of the new *Verbena* differed primarily from plants of 'Lan Depink' in the following characteristics:

1. Plants of the new *Verbena* were not as compact as plants of 'Lan Depink'.
2. Plants of the new *Verbena* had larger flowers than plants of 'Lan Depink'.

Plants of the new *Verbena* can also be compared to plants of the *Verbena hybrida* 'USBENAL5', disclosed in U.S. Plant Pat. No. 14,851. In side-by-side comparisons conducted in Bonsall, Calif., plants of the new *Verbena* differed primarily from plants of 'USBENAL5' in the following characteristics:

1. Flowers petals of plants of the new *Verbena* were more oblong than and not as round as flower petals of plants of 'USBENAL5'.
2. Plants of the new *Verbena* and 'USBENAL5' differed in flower color as plants of 'USBENAL5' had purple-colored flowers.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the actual colors of the new *Verbena* plant.

The photograph at the bottom of the sheet comprises a side perspective view of a typical flowering plant of 'AKIV98-01' grown in a container.

The photograph at the top of the sheet is a close-up view of typical flowers and leaves of 'AKIV98-01'.

DETAILED BOTANICAL DESCRIPTION

Plants used for the aforementioned photographs and following description were grown under conditions which closely approximate commercial production conditions during the autumn in 12.5-cm containers in an outdoor nursery in Bonsall, Calif. During the production of the plants, day temperatures ranged from 18° C. to 38° C., night temperatures ranged from 9° C. to 18° C. and light levels ranged from 7,000 to 10,000 foot-candles. Plants were pinched one time and were six weeks old when the photographs and description were taken. In the following description, color references are made to The Royal Horticultural Society Colour Chart, 2007 Edition, except where general terms of ordinary dictionary significance are used.

Botanical classification: *Verbena hybrida* 'AKIV98-01'.

Parentage:

- *Female, or seed, parent.*—*Verbena peruviana* 'Sunvivaro', disclosed in U.S. Plant Pat. No. 13,724.
- *Male, or pollen, parent.*—*Verbena hybrida* 'USBENAL17', disclosed in U.S. Plant Pat. No. 14,877.

Propagation:

- *Type cutting.*—Vegetative tip cuttings.
- *Time to initiate roots, summer.*—About three days at temperatures ranging from 17° C. to 29° C.
- *Time to initiate roots, winter.*—About four days at temperatures ranging from 17° C. to 21° C.
- *Time to produce a rooted plant, summer.*—About 15 days at temperatures ranging from 17° C. to 29° C.
- *Time to produce a rooted plant, winter.*—About 20 days at temperatures ranging from 17° C. to 21° C.
- *Root description.*—Medium in thickness, fibrous; off-white in color.
- *Rooting habit.*—Moderately freely branching; medium in density.

Plant description:

- *Plant habit.*—Initially upright, then low to outwardly spreading plant habit; freely branching habit with about twelve primary lateral branches developing per plant each with numerous secondary branches; pinching enhances lateral branch development; dense and bushy plant habit; vigorous growth habit.
- *Plant height.*—About 11 cm.
- *Plant diameter* (*spread*).—About 44 cm.

Lateral branch description:

- *Length.*—About 27 cm.
- *Diameter.*—About 2 mm.
- *Internode length.*—About 2.7 cm.
- *Strength.*—Strong.
- *Texture.*—Pubescent.
- *Color.*—Close to 146B.

Foliage description:

- *Arrangement.*—Opposite, simple.
- *Length.*—About 4.7 cm.
- *Width.*—About 2.8 cm.
- *Shape.*—Oblong to elliptical.
- *Apex.*—Broadly acute.
- *Base.*—Attenuate.
- *Margin.*—Irregularly crenate.
- *Texture, upper and lower surfaces.*—Pubescent; coarse, rough.
- *Venation pattern.*—Pinnate; reticulate.
- *Color.*—Developing leaves, upper surface: Close to 137B. Developing leaves, lower surface: Close to 147B. Fully expanded leaves, upper surface: Close to N137A; venation, close to 137A. Fully expanded leaves, lower surface: Close to 147B; venation, close to 147C.
- *Petiole.*—Length: About 7 mm. Diameter: About 2 mm. Texture, upper and lower surfaces: Pubescent. Color, upper and lower surfaces: Close to 146D.

Flower description:

- *Flower arrangement and habit.*—Salverform sessile flowers arranged in compact hemispherical terminal racemes; flowers face upward or outward; freely flowering habit with about 20 flowers per inflorescence.
- *Natural flowering season.*—Plants flower continuously from spring through the autumn in Southern California; plants begin flowering about six weeks after planting.
- *Flower longevity.*—Flowers last about five to seven days on the plant; flowers not persistent.
- *Fragrance.*—None detected.
- *Inflorescence height.*—About 3 cm to 3.5 cm.
- *Inflorescence diameter.*—About 5.5 cm.
- *Flower diameter.*—About 1.8 cm.
- *Flower depth* (*height*).—About 2.5 cm.
- *Flower buds.*—Length: About 2.2 cm. Diameter: About 4 mm. Shape: Elongates oblong. Color: Close to 186C.
- *Corolla.*—Arrangement: Single whorl of five fused petals fused towards the base into a narrow tube. Petal lobe length: About 8 mm to 10 mm. Petal lobe width: About 5 mm to 6 mm. Petal lobe shape: Roughly cordate. Petal lobe apex: Emarginate to cordate. Petal margin: Entire. Petal texture, upper and lower surfaces: Smooth, glabrous; velvety. Color: Petal, when opening, upper surface: Close to N57B. Petal, when opening, lower surface: Close to 62C. Petal, fully opened, upper surface: Close to 53C; towards the throat, close to 46A; color becoming closer to N57C with development. Petal, fully opened, lower surface: Close to N57D; color becoming closer to 62C with development. Tube: Close to 145D.
- *Calyx.*—Arrangement: Single whorl of five fused sepals fused towards the base into a narrow tube. Sepal length: About 1.5 cm. Sepal width: About 1 mm. Sepal shape: Narrowly lanceolate. Sepal apex: Acute. Sepal margin: Entire. Sepal texture, upper surface: Smooth, glabrous. Sepal texture, lower surface: Pubescent. Sepal color, upper and lower surfaces: Close to 146A.

*Peduncles.*—Length: About 5.2 cm. Diameter: About 2 mm. Strength: Strong. Texture: Pubescent. Color: Close to 146A.

*Reproductive organs.*—Stamens: Quantity/arrangement: Four per flower, filaments are adnate to corolla tube. Filament length: About 1.5 mm. Filament color: Close to 145D. Anther shape: Oval, bi-lobed. Anther length: About 1 mm. Anther color: Close to 2C. Pollen amount: Scarce. Pollen color: Close to 2A. Pistils: Quantity: One per flower. Pistil length: About 2.3 cm. Stigma shape: Rounded, slightly bi-parted. Stigma color: Close to 145A. Style length: About 1.8 cm. Style color: Close to 145C. Ovary color: Close to 146C. Fruits/seed: Fruit and seed development have not been observed.

Temperature tolerance: Plants of the new *Verbena* have been observed to tolerate temperatures from about 1° C. to about 40° C.

Pathogen/pest resistance:

Plants of the new *Verbena* have been observed to be tolerant to Powdery Mildew. Plants of the new *Verbena* have not been observed to be resistant to pests and other pathogens common to *Verbenas*.

It is claimed:

1. A new and distinct *Verbena* plant named 'AKIV98-01' as illustrated and described.

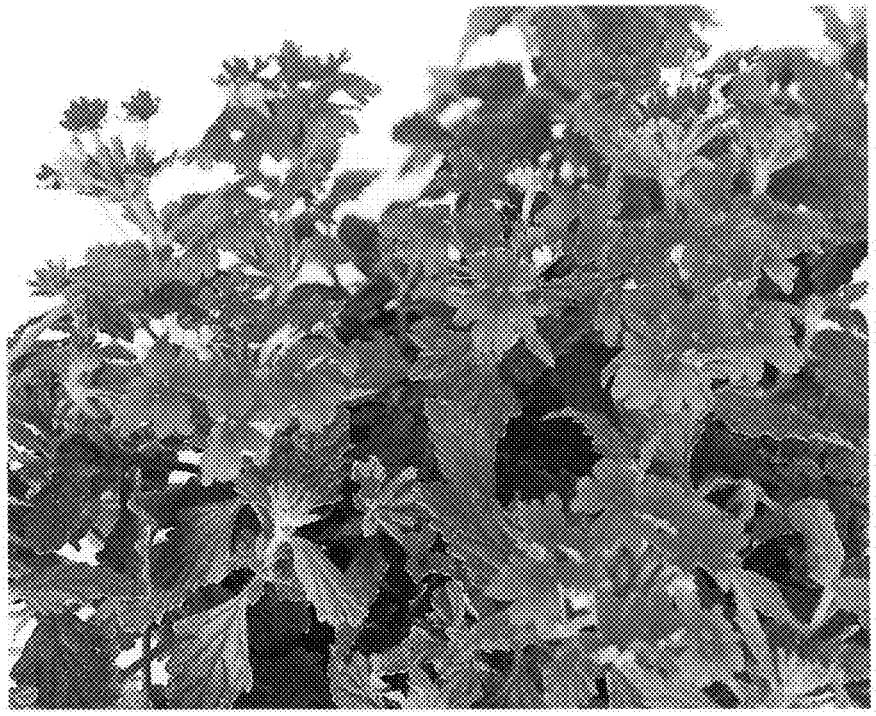
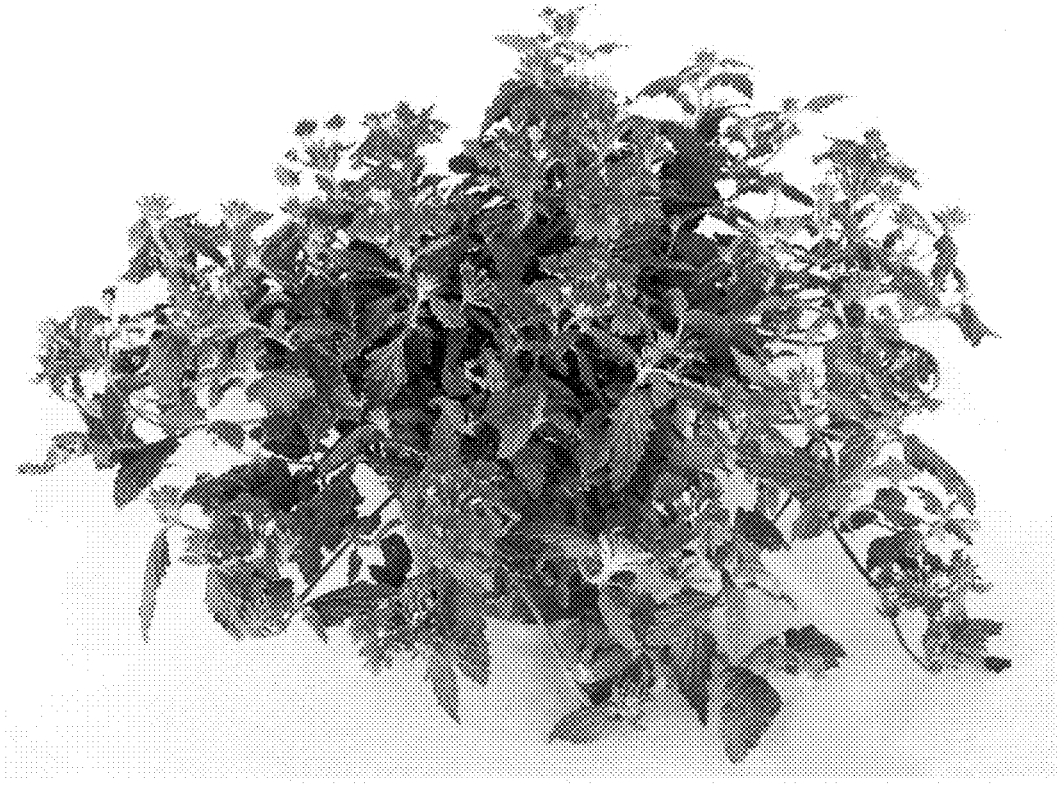

* * * * *